(12) United States Patent
Köhler et al.

(10) Patent No.: US 7,947,863 B2
(45) Date of Patent: May 24, 2011

(54) HYDROGELS OF HYDROPHILIC POLYURETHANE (METH)ACRYLATES

(75) Inventors: Burkhard Köhler, Kassel (DE); Michael Mager, Leverkusen (DE)

(73) Assignee: Bayer Material Science AG (DE)

( * ) Notice: Subject to any disclaimer, the term of this patent is extended or adjusted under 35 U.S.C. 154(b) by 143 days.

(21) Appl. No.: 12/008,939

(22) Filed: Jan. 15, 2008

(65) Prior Publication Data

US 2008/0177213 A1    Jul. 24, 2008

(30) Foreign Application Priority Data

Jan. 18, 2007  (DE) .......................... 10 2007 002 783

(51) Int. Cl.
*A61F 13/00* (2006.01)
*A61F 15/00* (2006.01)

(52) U.S. Cl. .......... 602/48; 424/443; 424/445; 604/304; 604/308

(58) Field of Classification Search .................... 602/48; 424/443, 445; 524/812, 813, 839; 526/301; 528/75; 522/97; 604/304–308

See application file for complete search history.

(56) References Cited

U.S. PATENT DOCUMENTS

| | | | |
|---|---|---|---|
| 4,780,512 A | 10/1988 | Gould et al. | |
| 4,954,587 A | 9/1990 | Mueller | 526/245 |
| 5,011,275 A | 4/1991 | Mueller | 351/160 H |
| 5,059,424 A | 10/1991 | Cartmell et al. | 424/443 |
| 5,112,618 A | 5/1992 | Cartmell et al. | 424/443 |
| 5,115,801 A | 5/1992 | Cartmell et al. | 602/48 |
| 5,145,906 A * | 9/1992 | Chambers et al. | 524/732 |
| 5,204,110 A | 4/1993 | Cartmell et al. | 424/443 |
| 5,932,352 A * | 8/1999 | Higgins | 428/423.1 |
| 6,013,750 A * | 1/2000 | Friese et al. | 526/301 |
| 6,180,132 B1 | 1/2001 | Huang et al. | 424/445 |
| 6,238,691 B1 | 5/2001 | Huang | 424/443 |
| 6,602,972 B1 * | 8/2003 | Schwarte et al. | 528/45 |
| 6,861,067 B2 * | 3/2005 | McGhee et al. | 424/445 |
| 2001/0026810 A1 | 10/2001 | McGhee et al. | 424/486 |
| 2005/0271727 A1 * | 12/2005 | Yao | 424/486 |
| 2006/0178071 A1 * | 8/2006 | Schmidt et al. | 442/417 |
| 2008/0199810 A1 * | 8/2008 | Narang et al. | 430/286.1 |

FOREIGN PATENT DOCUMENTS

| | | |
|---|---|---|
| GB | 2 086 927 A | 5/1982 |
| GB | 2 131 442 A | 6/1984 |
| GB | 2 150 938 A | 7/1985 |

OTHER PUBLICATIONS

J. Kim, et al., "Swelling behavior of novel polyurethane hydro-xerogels," *Polymer Bulletin*, vol. 36, No. 6, pp. 737-744 (1996).

B.K. Kim, et al., "UV-Curable Poly(ethylene glycol)-Based Polyurethane Acrylate Hydrogel," *Journal of Polymer Science: Part A: Polymer Chemisfty*, vol, 37, pp. 2703-2709 (1999).

* cited by examiner

*Primary Examiner* — Kim M Lewis
(74) *Attorney, Agent, or Firm* — Connolly Bove Lodge & Hutz LLP

(57) ABSTRACT

Processes for preparing polyurethane hydrogels which include free-radically cross-linking: A) hydrophilic polyurethanes having one or more olefinically unsaturated groups selected from the group consisting of acrylate and methacrylate groups; in the presence of B) water; and C) a redox system including a water-soluble oxidizing agent and a water-soluble reducing agent, the oxidizing agent being capable in terms of redox potential of reacting with the water-soluble reducing agent by free-radical formation, wherein the hydrophilic polyurethanes are based on hydroxyl-functional polyalkylene oxides.

10 Claims, No Drawings

HYDROGELS OF HYDROPHILIC POLYURETHANE (METH)ACRYLATES

CROSS-REFERENCE TO RELATED APPLICATION

This application claims priority under 35 U.S.C. §119(a-d) to German application No. DE 10 2007 003 783.6, filed Jan. 18, 2007.

FIELD OF THE INVENTION

The present invention relates to hydrogels formed from polyurethane (meth)acrylates in water using water-soluble redox initiators.

BACKGROUND OF THE INVENTION

Hydrogels are used for the medical treatment of wounds, being used in the form of appropriate wound contact materials particularly wherever keeping a wound moist leads to improved wound healing (moist wound treatment). Hydrogels are typically formed using synthetic polymers based on poly(meth)acrylates, polyvinylpyrrolidone or polyvinyl alcohol. In general, such hydrogels are notable for good compatibility with living tissue.

Also known are hydrogels of polyurethanes obtainable by reaction of hydrophilic, isocyanate-functional prepolymers and a large excess of water, as described for example in EP-A 426 422, EP-A 455324, WO 9817215, WO 9913923 and WO2002060501. The large excess of water is necessary to avoid foaming due to the carbon dioxide released by the reaction of isocyanate groups with water. This means, conversely, that polyurethane hydrogels having a low level of initially added water (bubble free) are not obtainable. Thus produced polyurethane hydrogels can therefore only give off water to a (dry) wound, whereas wound fluid can only be taken up to a very limited extent.

Moreover, prior art production of polyurethane hydrogels is a slow operation which frequently has to utilize three components and in which the resulting gel still contains large amounts of unbound polyol. The synthesis usually utilizes aliphatic, isocyanate-functional prepolymers based on a polyethylene glycol, polypropylene glycol or glycerol as polyol, partly in the presence of an accelerant, for example oligoalkylene oxides having primary amino end groups; that is, three components are necessary for faster-reacting systems. The polyol is utilized in distinctly superstoichiometric amounts. It follows that the hydrogels described still contain excess polyol and activator. Furthermore, reaction times are very slow, gel point often only being reached after 90 minutes. To what extent such gels can be additized with antimicrobially active substances has not been described to date.

There are also hydrogels that are formed by free-radical crosslinking. GB-A 2086927 describes semi-IPN hydrogels which, initiated by peroxides, are formed at elevated temperature by crosslinking of low molecular weight polyacrylates in the presence of an ethanolic solution of a linear polyurethane. Subsequently, the assistant solvent ethanol is removed.

GB-A 2131442 describes low molecular weight polyallyl compounds and GB 2150938 describes hydroxyethyl methacrylate (HEMA) and other monoacrylates as external, free-radically polymerizing monomers. These prior art references likewise involve an assistant solvent, such as ethanol, and peroxides at elevated temperature.

EP-A 351 364 describes hydrogels from N,N-dimethylacrylamide, fluorous polymers and crosslinkers, possible crosslinkers including polyols, such as polyvinyl alcohol or triethylene glycol, reacted with unsaturated isocyanates, such as MOI (methacryloyloxyethyl isocyanate) or TMI ($\alpha,\alpha$-dimethyl-3-isopropenylbenzyl isocyanate). Crosslinking was effected by initiation with UV or free-radical initiators. The same disadvantages as described above apply. Moreover, UV crosslinking in body contact is critical (reaction with the skin, eye protection for patient and for medical personnel).

US 2005 0271727 describes hydrogels formed by redox polymerization from polyvinyl alcohol and a crosslinker prepared, at some cost and inconvenience, from HEMA and glycolide according to Furch et al, Polymer, (1998) 39 (10), 1977-1982.

There is therefore a need for a polyurethane hydrogel which when needed can be formed using just small amounts of water and therefore is capable, when in contact with a wound, of additionally taking up wound fluid. Of course, the polyurethane hydrogel shall continue to be able to give off water to (dry) wounds. Since the polyurethane hydrogel is if necessary only formed in a wound or other body opening (in the case of endoscopic interventions for example), crosslinking has to take place without significant exotherm. The use of radiative curing (UV crosslinking for example) is to be avoided because of the high cost and inconvenience. All liquid precursors as well as the polyurethane hydrogel itself shall possess good biocompatibility; and the use of organic solvents shall be avoided.

SUMMARY OF THE INVENTION

It has now been found that aqueous solutions of hydrophilic polyurethane acrylates having molar masses of at least 2000 g/mol are crosslinkable by a redox system at temperatures of 10 to 42° C. and that the water content of the polyurethane hydrogel formed can be adjusted within wide limits. The use of organic solvents or of monomeric acrylates is not necessary; the polyurethane hydrogels obtained exhibit good biocompatibility.

The present invention accordingly provides a process for preparing polyurethane hydrogels which comprises free-radically crosslinking
A) hydrophilic polyurethanes having olefinically unsaturated groups in the presence of
B) water and
C) a redox system comprising a water-soluble oxidizing agent and a water-soluble reducing agent, the oxidizing agent being capable in terms of redox potential of reacting with the water-soluble reducing agent by free-radical formation.

The hydrogels thus obtainable form part of the subject matter of the present invention as well as the process for producing polyurethane hydrogels.

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein. If not indicated otherwise, percentages shall be understood as weight-%.

The essential hydrophilic polyurethanes having olefinically unsaturated groups are obtainable by reaction of polyisocyanates with hydroxyl-functional polyalkylene oxides.

These polyalkylene oxides preferably have an ethylene oxide content of at least 50% based on the oxyalkylene units present, more preferably at least 60%.

It is particularly preferable for these polyalkylene oxides to comprise copolymers of ethylene oxide and propylene oxide with an ethylene oxide content of 50 to 100%, preferably 60 to 82%, started on polyols or amines, such as water (considered as diol), ethylene glycol, propylene glycol, butylene glycol, glycerol, (TMP) timethylolpropane, sorbitol, pentaerythritol, triethanolamine, ammonia or ethylenediamine.

The molar masses of these polyalkylene oxides are preferably $M_n$=2000 to 20 000 g/mol, more preferably 4000 to 8500 g/mol.

The OH functionality is preferably 2 to 6, more preferably 3 to 6 and most preferably 3 to 4.

Useful polyisocyanates include, for one, olefinically unsaturated isocyanates, such as MOI (isocyanatoethyl methacrylate), TMI (3-isopropenyl-α,α-dimethylbenzyl isocyanate) or allyl isocyanate.

It is likewise possible to use saturated di- or polyisocyanates instead of or in addition to olefinically unsaturated di- or polyisocyanates and subsequently to introduce the olefinically unsaturated groups by reaction with compounds which have at least one isocyanate-reactive group besides the unsaturated group.

To this end, a prepolymer is prepared by reaction of a 1.6 to 30 times equivalent amount of diisocyanate based on the OH groups of the polyalkylene oxide. The NCO/OH ratio is preferably in the range from 4:1 to 12:1 and more preferably 2:1.

If appropriate, catalysts such as amines or tin compounds and/or stabilizers such as benzoyl chloride, isophthaloyl chloride, dibutyl phosphate, 3-chloropropionic acid or methyl tosylate can be added during the preparation.

The reaction temperature is in the range from 20 to 120° C. and preferably in the range from 60 to 100° C.

Excess, unreacted isocyanate can subsequently be removed, preferably by thin film distillation.

Suitable saturated diisocyanates conform to the general formula (I)

$$OCN—R—NCO \qquad (I),$$

where R is a $C_4$-$C_{22}$-alkylene radical, a $C_5$-$C_{22}$-cycloalkylene radical, a $C_8$-$C_{22}$-aralkylene radical wherein the carbon atoms linked to the isocyanate group are sp3 hybridized, or a $C_6$-$C_{18}$-aryl radical.

Examples of such diisocyanates are HDI, IPDI, bisisocyanatocyclohexylmethane, 2,2,4-trimethylhexamethylene diisocyanate, bisisocyanatomethylcyclohexane, bisisocyanatomethyltricyclodecane, xylylene diisocyanate, tetramethylxylylene diisocyanate, norbornane diisocyanate, cyclohexane diisocyanate, diisocyanatododecane, 2,4-TDI, 2,6-TDI, 2,2-, 2,4- or 4,4-MDI, 4,4'-diisocyanato-3,3'-dimethylbiphenyl, 3,4'-diisocyanatodiphenyl ether, 1,5-naphthylene diisocyanate or mixtures thereof.

However, the aliphatic diisocyanates of the aforementioned kind are preferable because the hydrolysis products of the resulting polyurethanes are generally recognized as safe by toxicologists.

Subsequently, the isocyanate-functional prepolymers thus contained are reacted with compounds having at least one isocyanate-reactive group besides the unsaturated group. Preferred isocyanate-reactive groups are amino or hydroxyl functions, preferably hydroxyl functions.

The equivalent ratio of NCO groups to NCO-reactive groups is preferably in the range from 1.5:1 to 1.0:1. An excess of NCO-reactive groups must be avoided, or unsaturated monomers will be left over. In the event of a deficiency of such compounds, remaining free NCO groups are removed by reaction with water or monools, such as methanol, ethanol or isopropanol before application.

Preferred compounds having olefinically unsaturated groups and at least one isocyanate-reactive group are preferably hydroxyacrylates and -methacrylates such as hydroxyethyl acrylates, hydroxyethyl methacrylate, hydroxypropyl acrylate, hydroxypropyl methacrylate, hydroxybutyl acrylate, hydroxybutyl methacrylate, glycerol diacrylate, glycerol dimethacrylate, glycerol monoacrylate monomethacrylate, glycerol monoallyl ether methacrylate, TMP diacrylate, TMP dimethacrylate, pentaerythritol triacrylate, pentaerythritol trimethacrylate, and any desired mixtures thereof.

The conversion to hydrophilic polyurethanes having olefinically unsaturated groups is carried out at temperatures of 20 to 80° C., preferably in the presence of polymerization inhibitors, such as hydroquinone, hydroquinone monoalkyl ethers, di-tert-butylcresol or methylenebis(tert-butylcresol), and of catalysts of the OH—NCO reaction, such as tin compounds or amines.

Water-soluble oxidizing agents are materials capable of oxidizing the materials recited under water-soluble reducing agents or other materials to form free radicals.

Useful water-soluble oxidizing agents include hydrogen peroxide and its inorganic salts, peroxides, hydroperoxides, such as tert-butyl hydroperoxide, percarboxylic acids, such as peracetic acid, perbenzoic acid, per-m-chlorobenzoic acid, monoperoxyphthalic acid, and their ammonium, alkali metal or alkaline earth metal salts, inorganic per acids, preferably in the form of their ammonium or alkali metal salts, such as perboric acid, percarbonic acid, peroxodisulphuric acid, peroxodiphosphoric acid, Caro's acid, periodic acid, permanganic acid, perrhenic acid, halogens or halogen-donating substances, hypohalides, sodium chlorite, cerium(IV) compounds, such as cerium ammonium nitrate, or metal ions in a higher oxidation state than the most stable in water, such as vanadium(V) compounds, manganese(III) salts, iron(III) salts, hexacyano(III) ferrates, cobalt(III) salts, silver(I) salts, potassium bromate or oxones. Ammonium peroxodisulphate, sodium peroxodisulphate and potassium peroxodisulphate are preferred.

Water-soluble reducing agents are materials capable of reducing the materials mentioned under water-soluble oxidizing agents to form free radicals.

Useful water-soluble reducing agents include ascorbic acid, isoascorbic acid, compounds containing vicinal OH groups, such as glycerol or sugar alcohols or sugar or oligo- or polysaccharides, reducing sugars, such as glucose, formaldehyde, glyoxal, glyoxalic acid, sodium sulphite, ammonium sulphite, potassium sulphite or the corresponding hydrogensulphites or bisulphites or metabisulphites, sulphite-aldehyde adducts, sodium thiosulphate, potassium thiosulphate, thiourea, hydroquinone, pyrogallol, gallic acid, oxalic acid and salts thereof, tartaric acid and salts thereof, malonic acid and salts thereof, formic acid and salts thereof, lactic acid and salts thereof, titanium(III) salicylaldoxim, sodium hypophosphite, derivatives of phosphorous, phosphonous or phosphinous acid, sodium toluenesulphinate, derivatives of sulphinous acid, such as Rongalit (sodium formaldehydesuloxylate), sodium dithionite, mercaptoethanol, cysteine and cysteine-containing peptides, cysteineamine, thioglycolic acid, 3-thiopropionic acid, sulphur dioxide, NADH, iodides, cobalt(II) salts or ethylenethiourea. Ascorbic acid is preferred.

One or more activators can be used in addition to the oxidizing and reducing agents. Preferred activators are transition metal salts which, like iron, can change their oxidation state in uneven steps. Iron salts are particularly preferred activators.

Preferred iron salts are iron(II) or iron(III) salts, such as iron(II) chloride, ammonium iron(II) sulphate, iron(II) sulphate, iron(II) sulphate, iron(III) chloride, iron(III) nitrate, iron(II) acetylacetonate, potassium hexacyano(II) ferrate, sodium hexacyano(II) ferrate, ammonium hexacyano(II) ferrate, potassium hexacyano(III) ferrate, sodium hexacyano(III) ferrate, ammonium hexacyano(III) ferrate, sodium nitroprossate, iron(II) D gluconate, iron(II) lactate, iron(II) iodide, iron(II) perchlorate, iron(III) perchlorate, iron(II) tetrafluoroborate or iron(III) tosylate, and complexing ligands, such as nitrilotriacetic acid or EDTA, can be added in addition.

In a preferred embodiment, A) utilizes 1.0 part by weight of the hydrophilic, unsaturated polyurethane, B) utilizes 0.2 to 19 parts by weight of water and C) utilizes 0.05% to 5% by weight, based on the sum total of the amounts of A) and B), of each of the water-soluble oxidizing agent and of the water-soluble reducing agent, as redox system.

When an activator is used, it is added in amounts of 0.00001% to 0.01% by weight and preferably 0.0001% to 0.001% by weight of transition metal salt based on the sum total of the amounts of A) and B).

The process of the present invention is preferably carried out by providing separate aqueous solutions of the oxidizing agent and the reducing agent respectively. The hydrophilic polyurethane to be crosslinked has been dispersed or dissolved in at least one of the two solutions. Crosslinking is initiated by combining the two solutions, if appropriate in the presence of an activator, which may be in a state of solution.

It is particularly preferable for both the solution of the oxidizing agent and the solution of the reducing agent to contain hydrophilic polyurethane in dissolved or dispersed form.

A satisfactory reaction rate to form the hydrogel can be observed below room temperature. Hydrogel production is preferably carried out at 5 to 100° C. and more preferably at 10 to 42° C.

The two solutions can be mixed using conventional mixing techniques.

In addition to the formers of the hydrogel, antibiotically active materials as described in WO 2002060501 can be added as well, in which case water-soluble materials are preferred. Care must be taken with regard to the possible interaction of these materials with the oxidizing or reducing agents in that a mutual destruction of the components is a possibility which renders any long-term storage before application impossible. However, antibiotically active materials can also take over the role of oxidizing or reducing agents as a whole or in part, such as peroxodisulphates, hydrogen peroxide, permanganate, silver(I) compounds, sulphites or aldehydes.

It is also possible to add thickeners, such as polyvinyl alcohol, methyl, hydroxyethyl, hydroxypropyl or carboxymethyl ethers of polysaccharides, such as cellulose or starch, polyvinylpyrrolidone, polyacrylic acid, methyl vinyl ether-MA copolymers, inorganic thickeners, such as silicas, aluminosilicates or aluminium hydroxides, polypeptides, polysaccharides, such as gum arabic or agar, chitosan, hyaluronic acid or polyurethane thickeners, in which case the thickeners can also take over the role of reducing agents as a whole or in part. Thickeners can be incorporated in advance in the aqueous solutions of the hydrophilic urethane acrylate, or alternatively only be added shortly before the reaction.

The polyurethane hydrogels of the present invention are useful as wound contact materials for example. As wound contact materials, the polyurethane hydrogels can either be formed directly on the skin or wound through crosslinking of one or more of the above-described components, or a prefabricated polyurethane hydrogel is applied, typically in the form of a sheetlike wound contact material.

The polyurethane hydrogels of the present invention are further useful as post surgical adhesion prevention (PSA) to prevent the undesired growing together of organs. It is of particular advantage here that the polyurethane hydrogel is prepared from one or more initially liquid components and thus can be metered into the body in the case of endoscopic interventions in particular. After application, the polyurethane hydrogel forms as a result of the crosslinking described.

Depending on the choice of the polyol component of the polyurethane, the polyurethane hydrogel produced therefrom can be biostable or biodegradeable. Particularly when used as PSA, the use of a biodegradeable polyurethane hydrogel is preferred.

Use is possible on humans and on animals.

EXAMPLES

Example 1

An initial charge at 60° C. of 93.75 g of a polyether having an ethylene oxide content of 63% and a propylene oxide content of 37% started on TMP (3-functional), 0.0625 g of methylenebis-tert-butylcresol (BKF) and 0.0625 g of DBTL was admixed with 10 g of methacryloyloxyethyl isocyanate, stirred for 4 h and left to stand at room temperature for 4 d.

Then, 10 g of this hydrophilic urethane acrylate and 0.2 g of ammonium peroxodisulphate were dissolved in 40 g of water and, separately, another 10 g of the hydrophilic urethane acrylate and 1 g of ascorbic acid were dissolved in 40 g of water to which 10 µl of a 3 percent solution of iron(II) chloride had been added. Then, the two portions were combined by brief stirring, and a hydrogel was obtained after 5 min.

Example 2

An initial charge of 200 g of HDI and 1 g of benzoyl chloride had 400 g of a polyether having an ethylene oxide content of 63% and a propylene oxide content of 37% started on TMP (3-functional) added to it dropwise at 80° C. within 2 h and was subsequently stirred for 1 h. Then, the excess HDI was distilled off by thin film distillation at 130° C. and 0.1 Torr to leave 420 g of a prepolymer having an NCO content of 2.75%. 153 g of this prepolymer, 0.1 g of BKF and 0.1 g of DBTL were admixed with 21.4 g of 3-(acryloyloxy)-2-hydroxypropyl ester methacrylate (glycerol monoacrylate monomethacrylate) at 60° C., allowed to cool down to room temperature and left to stand for 4 d.

Then, 10 g of this hydrophilic urethane acrylate and 0.2 g of ammonium peroxodisulphate were dissolved in 40 g of water and, separately, another 10 g of the hydrophilic urethane acrylate and 1 g of ascorbic acid were dissolved in 40 g of water to which 10 µl of a 3 percent solution of iron(II) chloride had been added. Then, the two portions were combined by brief stirring, and a hydrogel was obtained after 5 min.

Example 3

To 112 g of a hexafunctional sorbitol-started polyethylene oxide having a molar mass of 6740 g/mol were added 0.1 g of BKF and 0.1 g of DBTL followed by 15 g of MOI. The mixture was allowed to stand at room temperature for 7 days.

Then, 10 g of this hydrophilic urethane acrylate and 0.2 g of ammonium peroxodisulphate were dissolved in 40 g of water and, separately, another 10 g of the hydrophilic urethane acrylate and 1 g of ascorbic acid were dissolved in 40 g of water to which 10 μl of a 3 percent solution of iron(II) chloride had been added. Then, the two portions were combined by brief stirring, and a hydrogel was obtained after 5 min.

Example 4

An initial charge of 100 g of HDI and 2 g of benzoyl chloride at 80° C. had 1000 g of a tetrafunctional ethylenediamine-started polyether having an ethylene oxide content of 75% and a propylene oxide content of 25% and a molar mass of 4800 g/mol added to it dropwise within 2 h. Subsequently, the mixture was stirred at 80° C. for 6 h. Then, the HDI excess was removed by thin film distillation at 130° C. to obtain a prepolymer having an NCO content of 3.11%. 67.5 g of this prepolymer was admixed with 0.1 g of BKF, 0.1 g of DBTL and 6.5 g of hydroxyethyl methacrylate (HEMA).

Then, 10 g of this hydrophilic urethane acrylate and 0.2 g of ammonium peroxodisulphate were dissolved in 40 g of water and, separately, another 10 g of the hydrophilic urethane acrylate and 1 g of ascorbic acid were dissolved in 40 g of water to which 10 μl of a 3 percent solution of iron(II) chloride had been added. Then, the two portions were combined by brief stirring, and a hydrogel was obtained after 5 min.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing polyurethane hydrogels which comprises free-radically crosslinking
   A) hydrophilic polyurethanes having one or more olefinically unsaturated groups selected from the group consisting of acrylate and methacrylate groups in the presence of
   B) water and
   C) a redox system comprising a water-soluble oxidizing agent and a water-soluble reducing agent, the oxidizing agent being capable in terms of redox potential of reacting with the water-soluble reducing agent by free-radical formation, wherein the hydrophilic polyurethanes are based on hydroxyl-functional polyalkylene oxides.

2. Process according to claim 1, wherein the hydroxyl-functional polyalkylene oxides have an ethylene oxide content of at least 60% based on the oxyalkylene units present.

3. Process according to claim 1, wherein the hydroxyl-functional polyalkylene oxides have a molecular weight of $M_n$=2000 to 20 000 g/mol and an OH functionality of 2 to 6.

4. Process according to claim 1, wherein the hydrophilic polyurethanes are based on aliphatic or cycloaliphatic diisocyanates.

5. Process according to claim 1, wherein the redox system consists of at least one compound selected from the group consisting of ammonium peroxodisulphate, sodium peroxodisulphate and potassium peroxodisulphate as oxidizing agent and ascorbic acid as reducing agent.

6. Process according to claim 1, wherein iron salts are used as activators in addition to the redox system.

7. Process according to claim 1, wherein A) utilizes 1.0 part by weight of the hydrophilic, unsaturated polyurethane, B) utilizes 0.2 to 19 parts by weight of water and C) utilizes 0.05% to 5% by weight, based on the sum total of the amounts of A) and B), of each of the water-soluble oxidizing agent and of the water-soluble reducing agent, as redox system.

8. Process according to claim 1, wherein antibiotically active components are also added.

9. A polyurethane hydrogel prepared by the process according to claim 1.

10. A wound treatment contact material comprising a polyurethane hydrogel according to claim 9.

* * * * *